United States Patent
Wu et al.

(10) Patent No.: US 10,772,639 B2
(45) Date of Patent: Sep. 15, 2020

(54) OSTEOTOMY DEVICE WITH AN EXTRACORPOREAL ALIGNMENT COMPONENT

(71) Applicant: A Plus Biotechnology Company Limited, New Taipei (TW)

(72) Inventors: Kai-Hsing Wu, Taipei (TW); Hsiang Wei Lo, New Taipei (TW); Kun-Jhih Lin, Taichung (TW); Ping Sheng Yu, Taipei (TW)

(73) Assignee: A PLUS BIOTECHNOLOGY COMPANY LIMITED, New Taipei (TW)

( * ) Notice: Subject to any disclaimer, the term of this patent is extended or adjusted under 35 U.S.C. 154(b) by 148 days.

(21) Appl. No.: 15/853,887

(22) Filed: Dec. 25, 2017

(65) Prior Publication Data

US 2019/0150943 A1 May 23, 2019

(30) Foreign Application Priority Data

Nov. 22, 2017 (TW) .............................. 106140619 A

(51) Int. Cl.
| | |
|---|---|
| *A61B 17/15* | (2006.01) |
| *A61B 17/14* | (2006.01) |
| *A61B 17/80* | (2006.01) |
| *A61B 17/17* | (2006.01) |

(Continued)

(52) U.S. Cl.
CPC .......... *A61B 17/151* (2013.01); *A61B 17/142* (2016.11); *A61B 17/152* (2013.01); *A61B 17/1764* (2013.01); *A61B 17/8061* (2013.01); *A61B 17/8095* (2013.01); *A61B 17/157* (2013.01); *A61B 17/1767* (2013.01);
(Continued)

(58) Field of Classification Search
CPC .............. A61B 17/152; A61B 17/1767; A61B 17/1764; A61B 17/8095; A61B 17/151; A61B 17/157; A61B 17/809; A61B 17/8897
USPC ........................................... 606/87–88, 86 R
See application file for complete search history.

(56) References Cited

U.S. PATENT DOCUMENTS

| | | | | |
|---|---|---|---|---|
| 4,502,474 A | * | 3/1985 | Comparetto | ....... A61B 17/1637 606/87 |
| 5,601,565 A | * | 2/1997 | Huebner | ................ A61B 17/15 606/79 |

(Continued)

*Primary Examiner* — David W Bates
*Assistant Examiner* — Marcela I Shirsat
(74) *Attorney, Agent, or Firm* — Muncy, Geissler, Olds & Lowe, P.C.

(57) ABSTRACT

The present invention provides an osteotomy device with an extracorporeal alignment component comprising a first body component, a second body component and an extracorporeal alignment component. The first body component has an upper guide edge for forming a cutting track. The second body component has a lower guide edge disposed below the upper guide edge. A guide slot is formed between the upper guide edge and the lower guide edge for guiding the saw blade to cut. The guide slot has a connecting member for connecting the upper guide edge and the lower guide edge. The extracorporeal alignment component has an engaging member and at least one aiming hole. The engaging member is engaged with the connecting member. The aiming hole is used to confirm the direction of cutting.

9 Claims, 6 Drawing Sheets

(51) Int. Cl.
*A61B 17/88* (2006.01)
*A61F 2/46* (2006.01)

(52) U.S. Cl.
CPC ......... *A61B 17/809* (2013.01); *A61B 17/8897* (2013.01); *A61F 2/4657* (2013.01)

(56) References Cited

U.S. PATENT DOCUMENTS

| | | | | |
|---|---|---|---|---|
| 2002/0165552 | A1* | 11/2002 | Duffner | A61B 17/15 606/87 |
| 2005/0273112 | A1* | 12/2005 | McNamara | A61B 17/15 606/87 |
| 2008/0015603 | A1* | 1/2008 | Collazo | A61B 17/152 606/87 |
| 2008/0262500 | A1* | 10/2008 | Collazo | A61B 17/152 606/88 |

* cited by examiner

OSTEOTOMY DEVICE WITH AN EXTRACORPOREAL ALIGNMENT COMPONENT

TECHNICAL FIELD

The present invention generally relates to an osteotomy device, and more particularly, to an osteotomy device with an extracorporeal alignment component.

BACKGROUND

The joints are the most common friction parts of the body when the human body moves. For this reason, the body naturally developed a buffered cartilage to prevent injury on the human body caused by bone friction.

However, under the continuous development of science and technology, human average life-span continues to be extended. But the articular cartilage is gradually worn with the aging of body. It causes the occurrence of degenerative joint disease called osteoarthritis. For patients with knee osteoarthritis in the observation of the X-ray, surgeons can find the uneven of joint surface, narrowed joint cavity and bone spurs. These pathological phenomena will cause the patients to produce pain, swelling, joint deformation, stiffness and other symptoms. This is the inevitable trend of physiological aging, it seems that the older the more likely to encounter the disease.

Taking knee for example, most common treatment of knee osteoarthritis is to implant the artificial joint to replace the knee joint surfaces, but large amount of soft tissue and hard tissue should be removed from the femur, the tibia and the patella to provide the fixation of metal and polyethylene implants. Due to the wear of the polyethylene component, the longevity of the artificial joint replacement is up to twenty years, but often complicated by postoperative infection, osteolysis and bone resorption. Resulting in the possibility of a revision surgery. Furthermore, in early-stage knee osteoarthritis, only the medial articular surface is affected. It is not necessary to replace all articular surface by artificial knee component. High tibial osteotomy is an alternative option for patients with medial knee osteoarthritis.

High tibial osteotomy is performed by a bony cutting plane in the proximal tibia of the knee on the medial side and making an opening wedge by spreading the incision. Finally, the construct is supported by bone plate fixation. Thus the biomechanical axis of the low limb can be corrected. In this procedure, the cartilage and bone stock around the knee are preserved. For the patients with medial knee osteoarthritis, it is a good option for surgical treatment.

The success for high tibial osteotomy relies on an appropriate bone cut including the cutting position, direction, depth, and the spreading height of the incision which are related to the correction angle. This surgery is highly technical demanded. At present, the surgeons perform the procedure based upon preoperative roentgenology images and their experience without any reference or guiding device. Moreover, the condition of genu varum or deformity is different for each patient. The above-mentioned parameters are also different for each patient. A personalized surgical instruments is needed for a better control of the deformity correction.

The prior art of the present invention is TWM536526U. But, there is still room for improvement. For examples, it cannot take a non-invasive assessment of the correction angle when the surgery is performed, it cannot predict whether the angle of the osteotomy device placement is correct, it cannot directly fix the angle of the osteotomy device placement, it may produce an over-cutting phenomenon when starting to cut. The inventor of the present invention has further expanded its function and improved many of the techniques present in the prior art. Therefore, the inventor developed the osteotomy device with an extracorporeal alignment component, the expansion of the function and improvement of the technology will be described in detail in the specification.

SUMMARY OF THE INVENTION

In view of the foregoing problems, the present invention provides an osteotomy device with an extracorporeal alignment component. It is used to guide a saw blade to perform high tibial osteotomy of tibia, but not limited to, the osteotomy device with an extracorporeal alignment component can be used for other bones, such as: femur, fibula, humerus, ulna, radius, clavicle, scapula and so on. The tibia is described in the preferred embodiment of the present invention. The device design features to assist the surgeon to determine the cutting position, direction, depth, and the spreading height of the incision precisely. Moreover, it can take a non-invasive assessment of the angle during surgery, it can predict whether the angle/position of the osteotomy device placement is correct, it can directly maintain the angle/position of the osteotomy device placement and it can avoid over-cutting. The accuracy of the tibia osteotomy after the operation of the present invention will be improved. Each device is tailored to the patient.

The present invention provides an osteotomy device with an extracorporeal alignment component. The osteotomy device with an extracorporeal alignment component is used to guide a saw blade to perform high tibial osteotomy, but not limited to, it can also be applied to other bones. The osteotomy device with an extracorporeal alignment component comprises: a first body component, a second body component and an extracorporeal alignment component. Wherein the first body component has an upper guide edge for forming a cutting track; the second body component has a lower guide edge disposed below the upper guide edge, a guide slot is formed between the upper guide edge and the lower guide edge for guiding a saw blade to perform a cutting procedure. The guide slot has a connecting member for connecting the upper guide edge and the lower guide edge. The extracorporeal alignment component has an engaging member and at least one aiming hole. The engaging member is engaged with the connecting member. The aiming hole is used to confirm the direction of cutting.

According to the embodiment of the present invention, the first body component has an upper guide edge and a side guide edge. The side guide edge is disposed at the end of the upper guide edge for forming a cutting track.

According to the embodiment of the present invention, the second body component has a lower guide edge and an extended barrier plate. The lower guide edge disposed below the upper guide edge. The extended barrier plate is disposed at the end of the lower guide edge to prevent over-cutting by the saw blade on the side guide edge. A guide slot is formed between the upper guide edge and the lower guide edge for guiding a saw blade to perform a cutting procedure. The guide slot has a connecting member for connecting the upper guide edge and the lower guide edge.

According to the embodiment of the present invention, the extracorporeal alignment component has an engaging member, at least one aiming hole and an angle fixation hole. The engaging member is engaged with the connecting member. The aiming hole is used to confirm the direction of cutting. The angle fixation hole is disposed in the engaging member, the angle/position of the osteotomy device with an extracorporeal alignment component is fixed to the bone by using an angle fixation bone pin.

According to the embodiment of the present invention, the first body component has an upper guide edge, a side guide edge and a first correcting through-hole. The side guide edge is disposed at the end of the upper guide edge for forming a cutting track. The first correcting through-hole is connected to the first body component by a first bar.

According to the embodiment of the present invention, the second body component has a lower guide edge, an extended barrier plate and a second correcting through-hole. The lower guide edge disposed below the upper guide edge. The extended barrier plate is disposed at the end of the lower guide edge to prevent the over-cutting phenomenon by the saw blade on the side guide edge. The second correcting through-hole is connected to the second body component by a second bar. A guide slot is formed between the upper guide edge and the lower guide edge for guiding a saw blade to perform a cutting procedure. The guide slot has a connecting member for connecting the upper guide edge and the lower guide edge.

According to the embodiment of the present invention, there is a regulative angle between the longitudinal axes of the first correcting through-hole and the second correcting through-hole. When the open angle of the gap of the osteotomy is the same as that of the preoperative planning correction angle, the longitudinal axes of the first correcting through-hole and the second hole axis of the second correcting through-hole will coincide and pass through an alignment bar.

According to the embodiment of the present invention, the aiming hole confirms the direction of cutting by passing through at least one aiming bone pin.

According to the embodiment of the present invention, the surfaces of the first body component and the second body component have a plurality of fixed holes, the osteotomy device with an extracorporeal alignment component is fixed on the surface of the bone by inserting at least one fixed bone pins in the plurality of fixed holes.

Compared with the conventional technique, the osteotomy device with an extracorporeal alignment component is manufactured by three-dimensional printing (3D printing) according to the patient's skeletal data collected before the operation and evaluating the optimal surgical cutting position and angle. The device itself can fit the patient's any bones fully, such as: femur, fibula, humerus, ulna, radius, clavicle, scapula and so on. The surgeon can perform the first cutting position under the guide slot specified by the device. The guide slot allows the surgeon to perform the operation accurately. It also provides a reference for calculating the angle and depth of cutting. The side guide edge provides the surgical reference of the surgeon at the second cutting position. The extracorporeal alignment component can take a non-invasive assessment of the angle when the surgery is performed, it can predict whether the angle/position of the osteotomy device placement is correct and it can directly fix the osteotomy device on the bone. The extended barrier plate can avoid producing an over-cutting phenomenon when starting to cut. The present invention further improves the original osteotomy device.

The components, characteristics and advantages of the present invention may be understood by the detailed description of the preferred embodiments outlined in the specification and the drawings attached.

DETAILED DESCRIPTION

Some preferred embodiments of the present invention will now be described in greater detail. However, it should be recognized that the preferred embodiments of the present invention are provided for illustration rather than limiting the present invention. In addition, the present invention can be practiced in a wide range of other embodiments besides those explicitly described, and the scope of the present invention is not expressly limited except as specified in the accompanying claims. The layout of components may be more complicated in practice.

Figure 1:
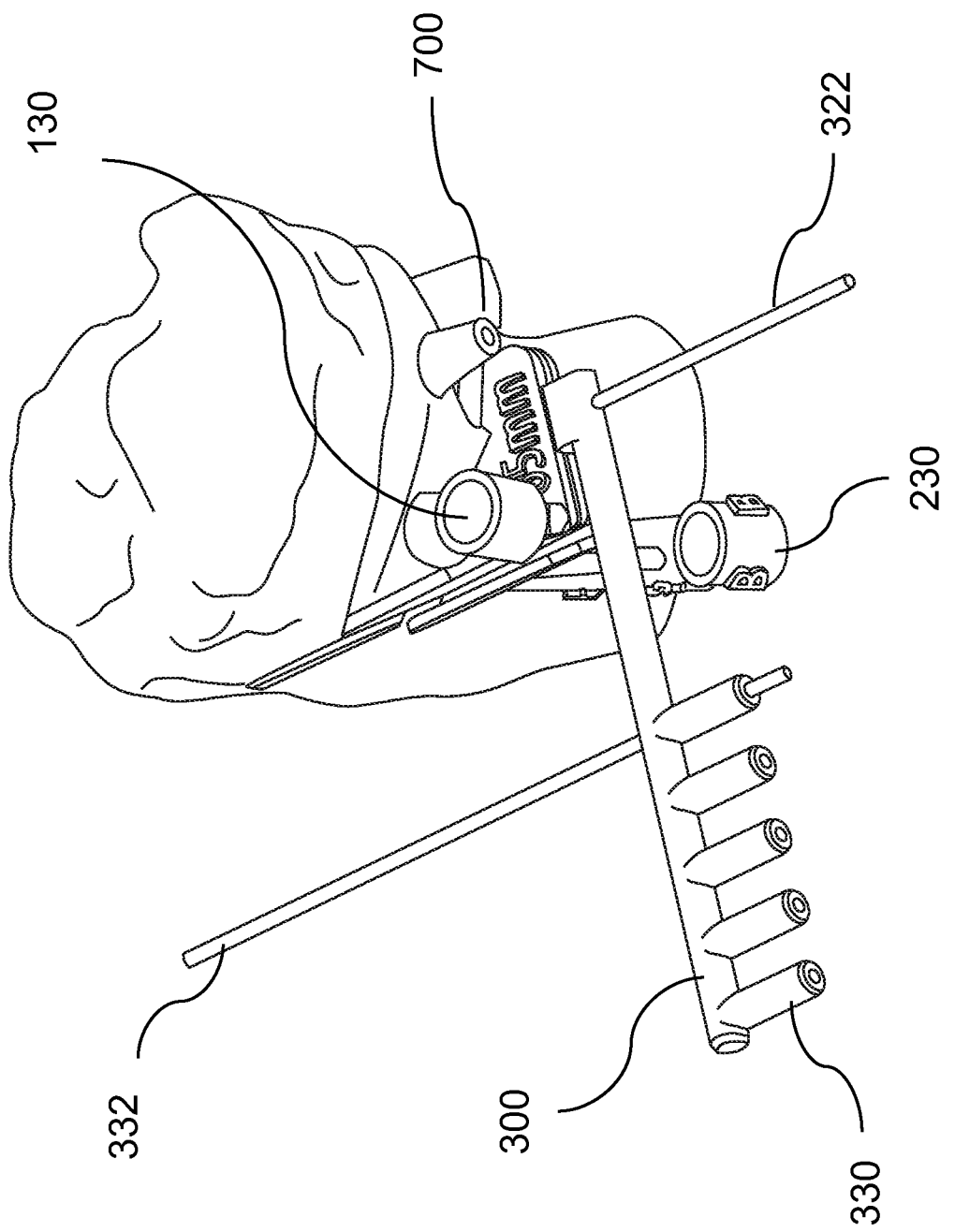
FIG. 1 illustrates a diagram of the osteotomy device with an extracorporeal alignment component placed on a bone.
Figure 2:
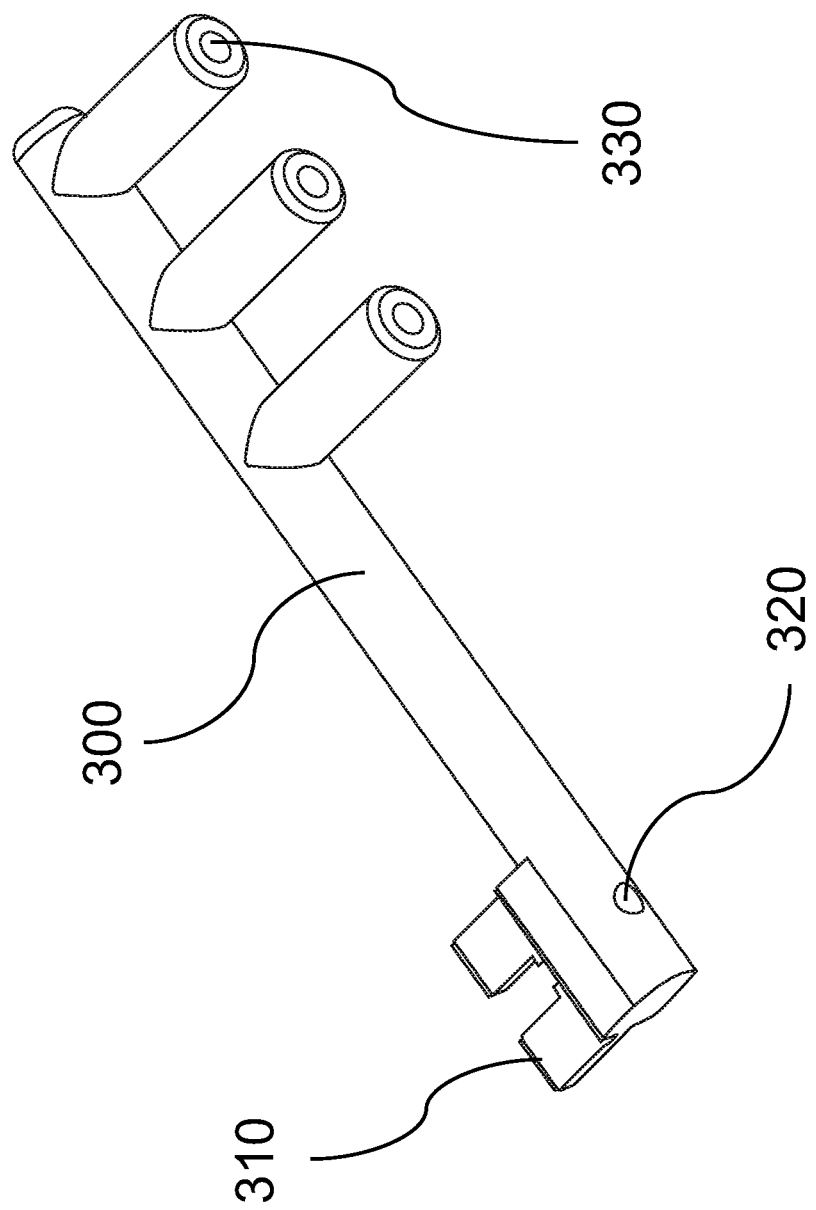
FIG. 2 illustrates a diagram of the extracorporeal alignment component.
Figure 3:
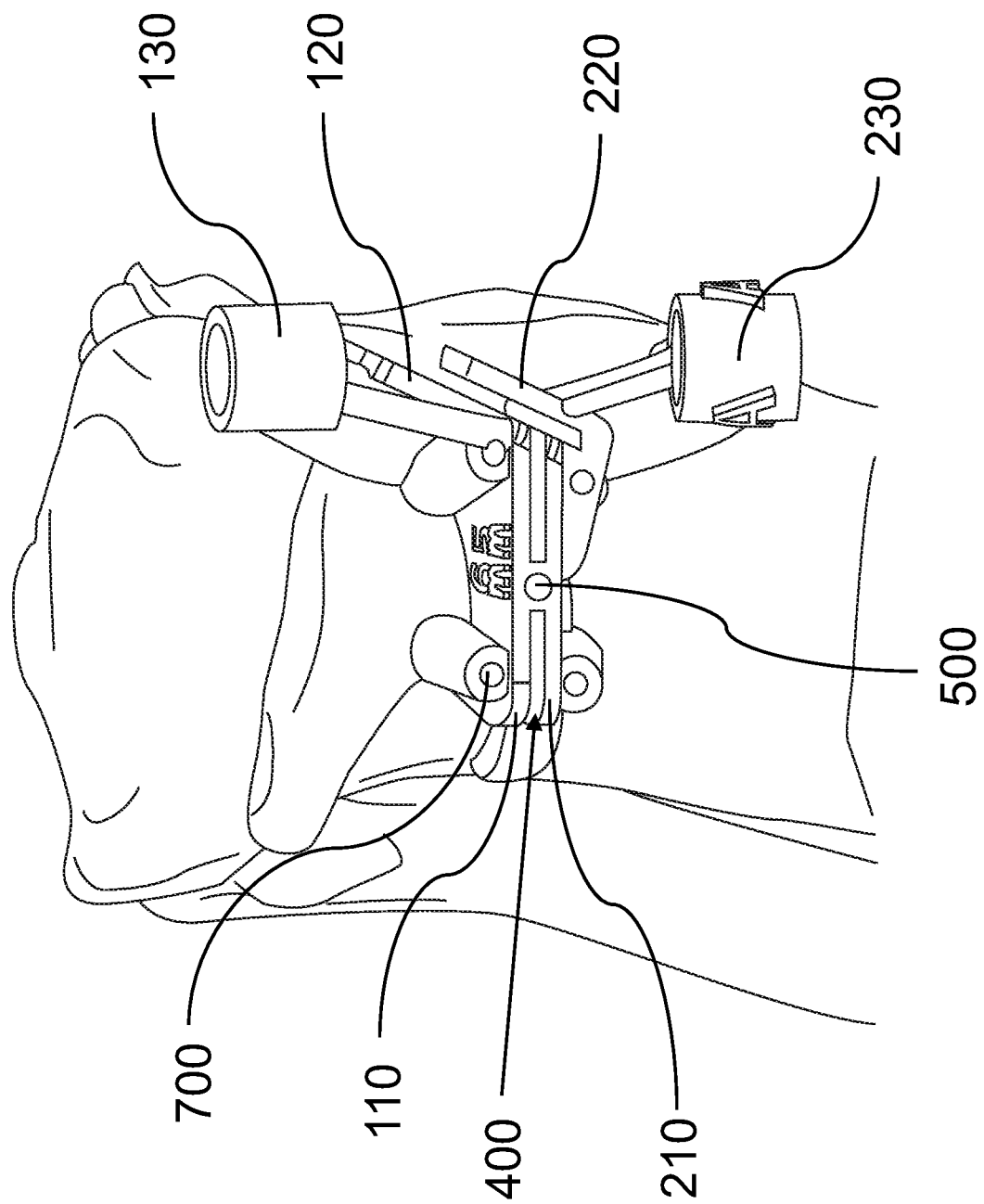
FIG. 3 illustrates a diagram of the osteotomy device without an extracorporeal alignment component.
Figure 4:
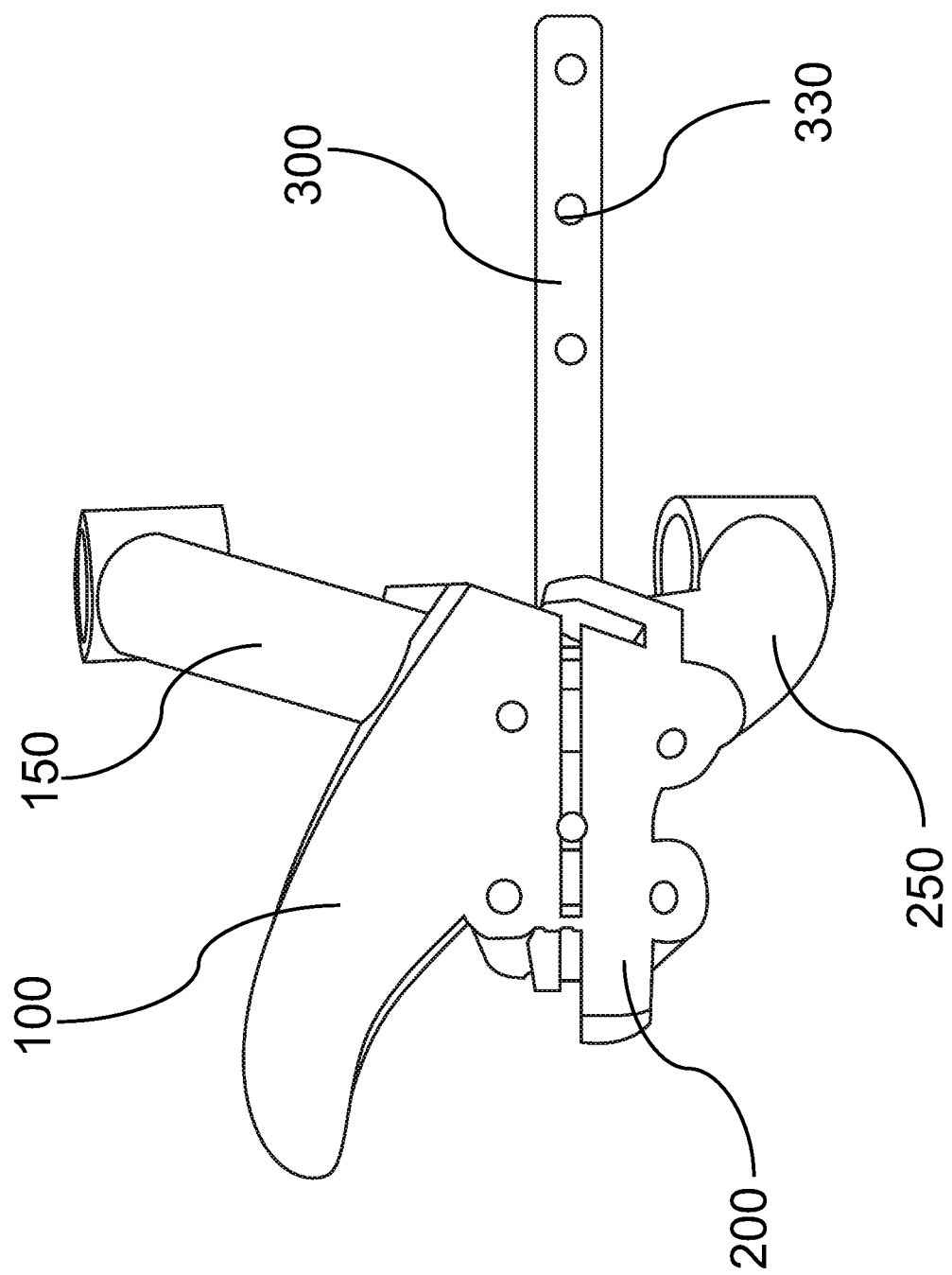
FIG. 4 illustrates a back view of the osteotomy device with an extracorporeal alignment component.

Please refer to FIG. 1, FIG. 2, FIG. 3 and FIG. 4. FIG. 1 illustrates a diagram of the osteotomy device with an extracorporeal alignment component placed on a bone. FIG. 2 illustrates a diagram of the extracorporeal alignment component 300. FIG. 3 illustrates a diagram of the osteotomy device without an extracorporeal alignment component 300. FIG. 4 illustrates a back view of the osteotomy device with an extracorporeal alignment component. The present invention provides an osteotomy device with an extracorporeal alignment component which can be used in various osteotomy, corrective operation or reduction surgery. The osteotomy device with an extracorporeal alignment component can be used for other bones, such as: femur, fibula, humerus, ulna, radius, clavicle, scapula and so on. In the present embodiment, the osteotomy device with an extracorporeal alignment component is used to guide a saw blade to perform high tibial osteotomy of tibia. The osteotomy device with an extracorporeal alignment component comprises: a first body component 100, a second body component 200 and an extracorporeal alignment component 300. Wherein the first body component 100 has an upper guide edge 110 for forming a cutting track; the second body component 200 has a lower guide edge 210 disposed below the upper guide edge 110, a guide slot 400 is formed between the upper guide edge 110 and the lower guide edge 210 for guiding a saw blade to perform a cutting procedure. The guide slot 400 has a connecting member 500 for connecting the upper guide edge 110 and the lower guide edge 210. The extracorporeal alignment component 300 has an engaging member 310 and at least one aiming hole 330. The engaging member 310 is engaged with the connecting member 500. The aiming hole 330 is used to confirm the direction of cutting. When the operation is performed, the surgeon can directly cut the connecting member 500 with the bone saw.

When the osteotomy device with an extracorporeal alignment component is arranged on the surface of patient's tibia, the extracorporeal alignment component 300 is mounted on the connecting member 500 of the osteotomy device with an extracorporeal alignment component through the engaging member 310. The engaging member 310 and the aiming hole 330 are respectively located at both ends of the extracorporeal alignment component 300. When the osteotomy device with an extracorporeal alignment component is placed on the bone surface, the extracorporeal alignment component 300 has a rectangular appearance and it is placed laterally on the osteotomy device with an extracorporeal alignment component so that the aiming hole 330 can be located outside the human body. The angle of placement of the osteotomy device with an extracorporeal alignment component can be evaluated in a noninvasive manner by the aiming hole 330. Therefore, it is possible to predict whether the angle of the osteotomy device with an extracorporeal alignment component is correct. Then, the surgeon inserts the saw blade and starts cutting according to the cutting position guided by the upper guide edge 110 and the lower guide edge 210 of the osteotomy device with an extracorporeal alignment component. The surgeon can use the upper guide edge 110 and the lower guide edge 210 as a reference for the calculation of the depth of cut. In another way, make a mark on the saw blade, the user can use the naked eye to confirm whether the depth of the saw blade cut into the tibia reached the preset depth.

In one embodiment of the present invention, the first body component 100 has an upper guide edge 110 and a side guide edge 120. The side guide edge 120 is disposed at the end of the upper guide edge 110 for forming a cutting track. The upper guide edge 110 and the lower guide edge 210 extend outwardly from the first body component 100 and the second body component 200, respectively. A guide slot 400 is formed between the upper guide edge 110 and the lower guide edge 210 for guiding the saw blade to perform a cutting procedure of the first cutting position. The side guide edge 120 is used to guide the saw blade to perform a cutting procedure of the second cutting position. The upper guide edge 110, the lower guide edge 210 and the side guide edge 120 are used to form the cutting track for operating high tibial osteotomy.

The surgeon can use the upper guide edge 110 and the lower guide edge 210 as a reference for the calculation of the depth of cut. The saw blade cuts to a predetermined depth and cuts along the upper guide edge 110 and the lower guide edge 210 to the inside of the human body. Then, it cuts off part of the tibia and cuts along the second cutting position guided by the side guide edge 120 to produce an oblique incision.

In one embodiment of the present invention, the second body component 200 has a lower guide edge 210 and an extended barrier plate 220. The lower guide edge 210 disposed below the upper guide edge 110. The extended barrier plate 220 is disposed at the end of the lower guide edge 210 to prevent the over-cutting phenomenon by the saw blade on the side guide edge 120. A guide slot 400 is formed between the upper guide edge 110 and the lower guide edge 210 for guiding a saw blade to perform a cutting procedure. The guide slot 400 has a connecting member 500 for connecting the upper guide edge 110 and the lower guide edge 210. In the previous technology of osteotomy device, it is found that the position of the side guide edge 120 often occurs an over-cutting phenomenon in the clinical operation. If the surgeon cuts more than a lot, the extra incision will make the bones become more fragile. It may cause bones to break when fixing the bone plate. So that the patient's recovery period is prolonged. In order to avoid the over-cutting phenomenon, the present invention further improves the design. An extended barrier plate 220 is added to the second body component 200 relative to the side guide edge 120. When the saw blade cuts to a predetermined position, it can be blocked by the extended barrier plate 220 to avoid the over-cutting phenomenon. The entire cutting track becomes complete. In the practice of osteotomy, the present invention is carried out more precisely in accordance with the originally intended plan. It can prevent the occurrence of defects and shorten the recovery period of patients.

In another embodiment of the present invention, the extracorporeal alignment component 300 has an engaging member 310, at least one aiming hole 330 and an angle fixation hole 320. The engaging member 310 is engaged with the connecting member 500. The aiming hole 330 is used to confirm the direction of cutting. The angle fixation hole 320 is disposed in the engaging member 310, the angle/position of the osteotomy device with an extracorporeal alignment component is fixed to the bone by using an angle fixation bone pin 322. When the aiming hole 330 confirms that the angle/position of the osteotomy device with an extracorporeal alignment component is correct, the osteotomy device with an extracorporeal alignment component can be fixed the angle/position on the bone directly by inserting the angle fixation bone pin 322 from the angle fixation hole 320 of the extracorporeal alignment component 300. Compared with the osteotomy device in the prior art, the present invention will have a more precise cutting angle and position. The precise cutting is a very important point in osteotomy. Because the open angle of the bone is based on it. Therefore, it will affect the ability to properly correct the biomechanical axis of the patient's knee.

Figure 5:
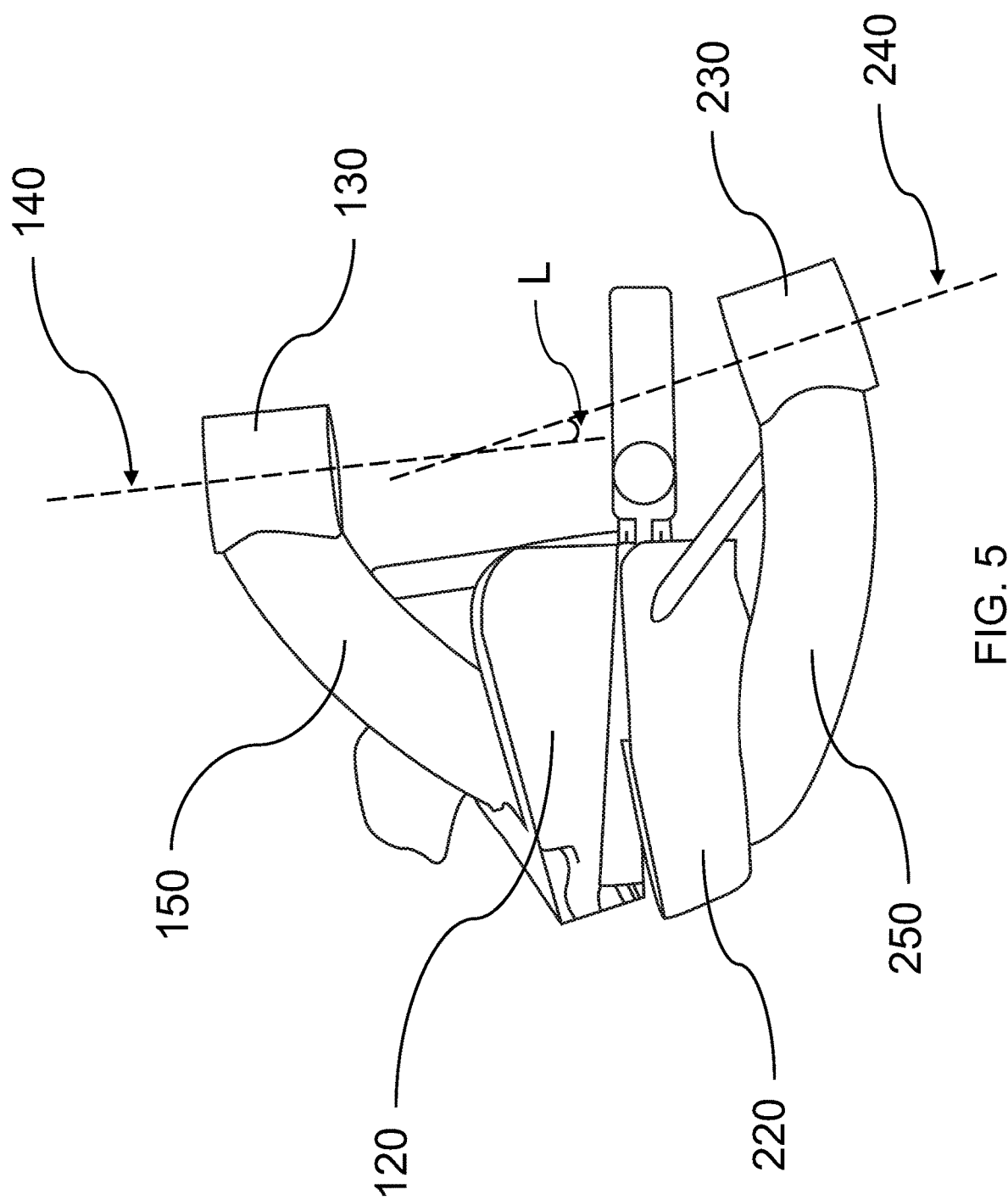
FIG. 5 illustrates a side view of the osteotomy device with an extracorporeal alignment component before surgical cutting.
Figure 6:
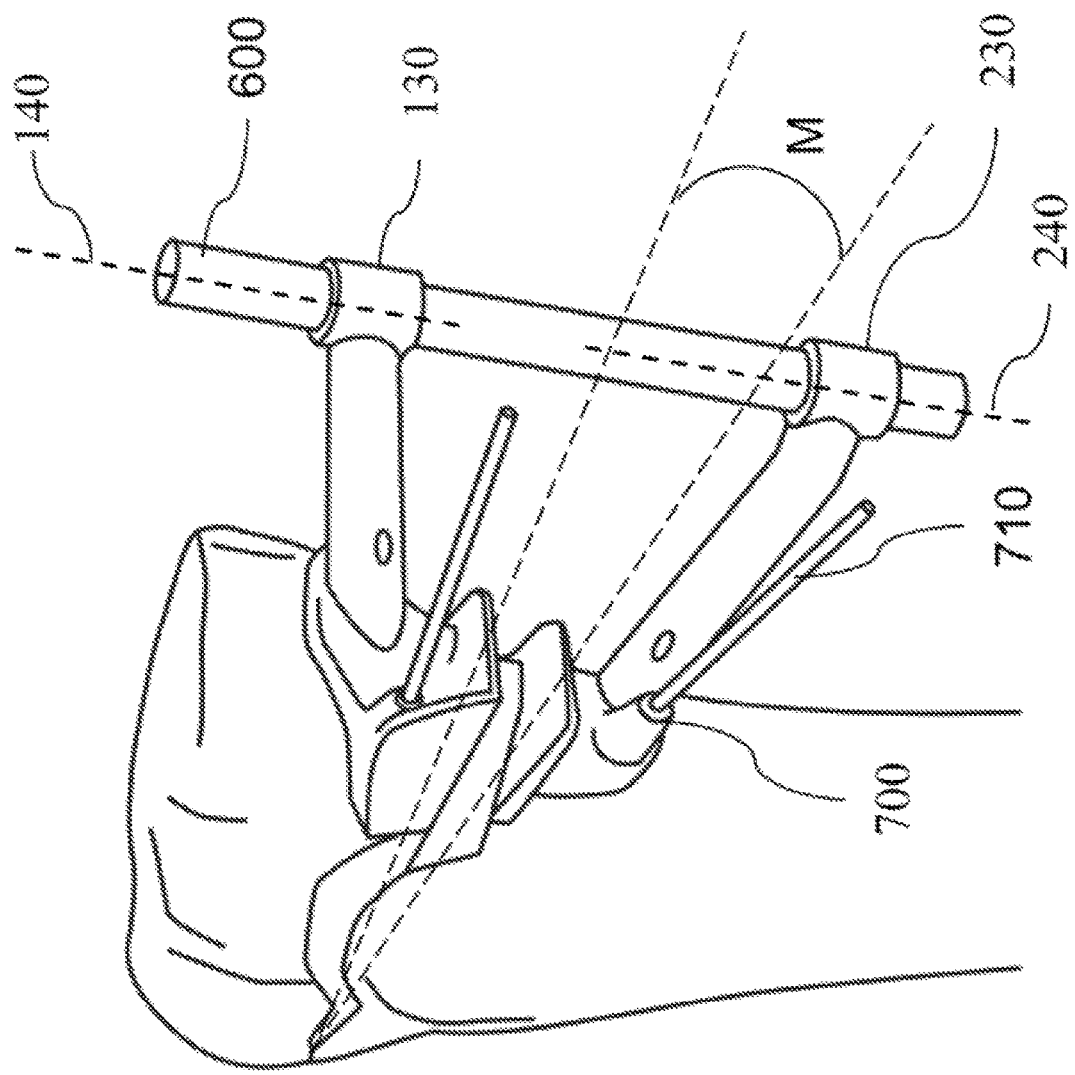
FIG. 6 illustrates that the bone is opened to the correction angle by the first body component and the second body component after surgical cutting.

Please refer to FIG. 5 and FIG. 6. FIG. 5 illustrates a side view of the osteotomy device with an extracorporeal alignment component. FIG. 6 illustrates that the bone is opened to the correction angle M by the first body component 100 and the second body component 200. In one embodiment of the present invention, the first body component 100 further comprises a first correcting through-hole 130. The first correcting through-hole 130 is connected to the first body component 100 by a first bar 150. The second body component 200 further comprises a second correcting through-hole 230. The second correcting through-hole 230 is connected to the second body component 200 by a second bar 250. In the present invention, the first correcting through-hole 130 and the second correcting through-hole 230 are designed to confirm the angle at which the tibial incision is opened in high tibial osteotomy. For this reason, there is a regulative angle L between the longitudinal axes 140 of the first correcting through-hole 130 and the second hole axis 240 of the second correcting through-hole 230. In high tibial osteotomy, a gap of the osteotomy has a preoperative planning correction angle M. When the tibia is opened by the first body component 100 and the second body component 200 with the correction angle M, the longitudinal axes 140 of the first correcting through-hole 130 and the second hole axis 240 of the second correcting through-hole 230 can coincide. An alignment bar 600 is passed through the first correcting through-hole 130 and the second correcting through-hole 230 to ensure the correction angle M. Firstly, the size of the aforementioned correction angle M is based on the correction angle M that the tibia needs to open in high tibial osteotomy. Secondly, the angle between the axis of the first correcting through-hole 130 and the axis of the second correcting through-hole 230 is determined according to the desired correction angle M and it is made. The alignment bar 600 can be inserted between the first correcting through-hole 130 and the second correcting through-hole 230 only when the tibia is opened at a preoperative planned correction angle M by the first body component 100 and the second body component 200.

The saw blade cuts to a predetermined depth and cut along the upper guide edge 110 and the lower guide edge 210 to the inside of the human body. Then, it cuts off part of the tibia and cuts along the second cutting position guided by the side guide edge 120 to produce an oblique incision. After the incision is cut, the first cutting position of the tibia is opened to the correction angle M of preoperative planning in the case where the osteotomy device with an extracorporeal alignment component is fixed to the tibia. The alignment bar 600 is then inserted through the first correcting through-hole 130 and the second correcting through-hole 230. After confirming the correction angle M of the surgical incision of the tibia, the gap can be fixed to complete the operation. The present invention can avoid ligament injury during surgery. It can also cut out an incision to resist the rotation of the bones due to the movement. The present invention is designed according to a preoperative correction plan so that the surgical procedure can be simplified.

In one embodiment of the present invention, the extracorporeal alignment component 300 has an engaging member 310 and at least one aiming hole 330. The engaging member 310 is engaged with the connecting member 500. The aiming hole 330 confirms the direction of cutting by passing through at least one aiming bone pin 332. The aiming hole 330 is cylindrical in the present embodiment, but not limited to, it may be changed to other shapes as necessary. The aiming hole 330 is sequentially attached to the extracorporeal alignment component 300 by an end of the extracorporeal alignment component 300. Its cylindrical design allows the aiming bone pin 332 to pass through. It is possible to determine whether the osteotomy device with an extracorporeal alignment component of the present invention is set at the correct angle/position by the guidance of the aiming bone pin 332. The aiming bone pin 332 is the guideline of the angle extracorporeal. It does not need to invade the body. Therefore, it can reduce the burden on patients.

In another embodiment of the present invention, the surfaces of the first body component 100 and the second body component 200 have a plurality of fixed holes 700, the osteotomy device with an extracorporeal alignment component is fixed on the surface of the bone by inserting at least one fixed bone pins 710 in the plurality of fixed holes 700. In order to reinforce the fixation strength of the osteotomy device with an extracorporeal alignment component on the bone surface, at least one fixed bone pins 710 may be inserted in the fixed holes 700 after the osteotomy device with an extracorporeal alignment component is fixed the angle/position on the bone directly by inserting the angle fixation bone pin 322 from the angle fixation hole 320 of the extracorporeal alignment component 300. Whereby the osteotomy device with an extracorporeal alignment component is fixed more firmly to the surface of the bone. It can avoid the saw blade causing the osteotomy device with an extracorporeal alignment component to move at the time of cutting. It makes the cutting position more accurate.

Compared with the conventional technique, the osteotomy device with an extracorporeal alignment component is manufactured by three-dimensional printing according to the patient's skeletal data collected before the operation and evaluating the optimal surgical cutting position and angle. The present invention is based on the different skeletal angles of each patient to create the overall structure of the osteotomy device with an extracorporeal alignment component. It constructs an integrally formed or combined solid instrument. The device itself can fit the patient's bones fully. The surgeon can perform the first cutting position under the guide slot 400 specified by the device. The guide slot 400 allows the surgeon to perform the operation accurately. It also provides a reference for calculating the angle and depth of cutting. The side guide edge 120 provides the surgical reference of the surgeon at the second cutting position. The extracorporeal alignment component 300 and the extended barrier plate 220 further improve the osteotomy device in the prior art. Therefore, the present invention can take a non-invasive assessment of the angle when the surgery is performed, it can predict whether the angle/position of the osteotomy device placement is correct, it can directly fix the osteotomy device and it can avoid producing an over-cutting phenomenon when starting to cut. In addition to improving the surgery itself, the present invention also standardizes the implementation of the surgeon's operation.

Various terms used in this disclosure should be construed broadly. For example, if an element "A" is to be coupled to or with element "B," element A may be directly coupled to element B or be indirectly coupled through, for example, element C. When the specification states that a component, feature, structure, process, or characteristic A "causes" a component, feature, structure, process, or characteristic B, it means that "A" is at least a partial cause of "B" but that there may also be at least one other component, feature, structure, process, or characteristic that assists in causing "B." If the specification indicates that a component, feature, structure, process, or characteristic "may", "might", or "could" be included, that particular component, feature, structure, process, or characteristic is not required to be included. If the specification refers to "a" or "an" element, this does not mean there is only one of the described elements.

The foregoing descriptions are preferred embodiments of the present invention. As is understood by a person skilled in the art, the aforementioned preferred embodiments of the present invention are illustrative of the present invention rather than limiting the present invention. The present invention is intended to cover various modifications and similar arrangements included within the spirit and scope of the appended claims, the scope of which should be accorded the broadest interpretation so as to encompass all such modifications and similar structures.

We claim:
1. An osteotomy device comprising:
   a first body component having an upper guide edge for forming a cutting track;
   a second body component having a lower guide edge disposed below said upper guide edge,
   a guide slot being formed between said upper guide edge and said lower guide edge for guiding a saw blade to perform a cutting procedure, said guide slot having a connecting member for connecting said upper guide edge and said lower guide edge;
   an alignment component comprising an engaging member and at least one aiming hole, said engaging member being engaged with said connecting member, said aiming hole being located at one end of the alignment component and configured to confirm a direction of cutting by at least one aiming bone pin passing through said aiming hole,
   wherein said alignment component has a long strip appearance and is placed on the osteotomy device in a plane that is the same as a surgical cutting plane, wherein the aiming hole is physically configured to be extracorporeal.

2. The osteotomy device of claim 1, said first body component further comprising:
a side guide edge being disposed at an end of said upper guide edge for forming the cutting track.

3. The osteotomy device of claim 2, said second body component further comprising:
an extended barrier plate being disposed at an end of said lower guide edge to prevent an over-cutting phenomenon by said saw blade on said side guide edge.

4. The osteotomy device of claim 1, said alignment component further comprising:
an angle fixation hole being disposed in said engaging member, an angle of said osteotomy device with the alignment component being fixed to said same plane as the surgical cutting plane by using an angle fixation bone pin.

5. The osteotomy device of claim 1, said first body component further comprising:
a first correcting through-hole being connected to said first body component by a first bar.

6. The osteotomy device of claim 5, said second body component further comprising:
a second correcting through-hole being connected to said second body component by a second bar.

7. The osteotomy device of claim 6, wherein a regulative angle between a longitudinal axis of said first correcting through-hole and a second hole axis of said second correcting through-hole is formed.

8. The osteotomy device of claim 7, when an open angle of a gap of an osteotomy is the same as that of a preoperative planning correction angle, said longitudinal axis of said first correcting through-hole and said second hole axis of said second correcting through-hole will coincide and pass through an alignment bar which can be inserted between said first correcting through-hole and said second correcting through-hole.

9. The osteotomy device of claim 1, wherein said first body component and said second body component have a plurality of fixed holes, said osteotomy device with the alignment component is fixed on the same plane as the surgical cutting plane by inserting at least one fixed bone pins in said plurality of fixed holes.

* * * * *